US008933227B2

(12) United States Patent
Linz et al.

(10) Patent No.: US 8,933,227 B2
(45) Date of Patent: Jan. 13, 2015

(54) SELECTIVE SYNTHESIS OF FUNCTIONALIZED PYRIMIDINES

(75) Inventors: Guenter Linz, Mittelbiberach (DE); Gerd Kraemer, Eberhardzell (DE); Sabrina Kusserow, Biberach an der Riss (DE); Juergen Schnaubelt, Oberhoefen/Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/853,732

(22) Filed: Aug. 10, 2010

(65) Prior Publication Data

US 2011/0190499 A1 Aug. 4, 2011

(30) Foreign Application Priority Data

Aug. 14, 2009 (EP) ..................................... 09167934

(51) Int. Cl.
*C07D 239/34* (2006.01)
*C07D 239/47* (2006.01)
*C07D 239/02* (2006.01)
*C07D 401/12* (2006.01)

(52) U.S. Cl.
CPC ............ *C07D 239/47* (2013.01); *C07D 401/12* (2013.01); *C07D 239/34* (2013.01)
USPC ...................................................... 544/332

(58) Field of Classification Search
None
See application file for complete search history.

(56) References Cited

U.S. PATENT DOCUMENTS

| | | | |
|---|---|---|---|
| 7,122,670 B2 | 10/2006 | Kath et al. | |
| 7,928,109 B2 | 4/2011 | Luzzio et al. | |
| 8,334,383 B2 | 12/2012 | Duran et al. | |
| 8,372,974 B2 | 2/2013 | Linz et al. | |
| 2006/0183694 A1 | 8/2006 | Sin et al. | |
| 2009/0163467 A1 | 6/2009 | Zahn et al. | |
| 2009/0306067 A1 | 12/2009 | Engelhardt et al. | |
| 2011/0060141 A1 | 3/2011 | Linz et al. | |
| 2011/0077403 A1 | 3/2011 | Duran et al. | |
| 2011/0190499 A1 | 8/2011 | Linz et al. | |
| 2012/0172596 A1 | 7/2012 | Linz et al. | |
| 2013/0079518 A1 | 3/2013 | Linz et al. | |
| 2014/0213787 A1 | 7/2014 | Linz et al. | |

FOREIGN PATENT DOCUMENTS

| | | | |
|---|---|---|---|
| JP | 62000062 | | 1/1987 |
| JP | 2004502763 A | | 1/2004 |
| JP | 2005527622 A | | 9/2005 |
| JP | 2008530096 A | | 8/2008 |
| WO | 0204429 A1 | | 1/2002 |
| WO | 03030909 A1 | | 4/2003 |
| WO | 03051119 A1 | | 6/2003 |
| WO | 03099771 A2 | | 12/2003 |
| WO | 2004048343 A1 | | 6/2004 |
| WO | 2005023780 A1 | | 3/2005 |
| WO | 2005026130 A1 | | 3/2005 |
| WO | 2006044823 A2 | | 4/2006 |
| WO | 2006099974 A1 | | 9/2006 |
| WO | 2006117560 A1 | | 11/2006 |
| WO | 2007072158 A2 | | 6/2007 |
| WO | 2007115999 A1 | | 10/2007 |
| WO | 2007132010 A1 | | 11/2007 |
| WO | 2008046216 A1 | | 4/2008 |
| WO | 2008046757 A1 | | 4/2008 |
| WO | 2008071587 A2 | | 6/2008 |
| WO | WO2008071587 | * | 6/2008 |
| WO | 2008079346 A1 | | 7/2008 |
| WO | 2008079719 A1 | | 7/2008 |
| WO | 2008129380 A1 | | 10/2008 |
| WO | WO2009115583 | * | 3/2009 |
| WO | 2009079412 A2 | | 6/2009 |
| WO | 2009115583 A1 | | 9/2009 |
| WO | 2009115587 A1 | | 9/2009 |
| WO | 2011018517 A1 | | 2/2011 |
| WO | 2011018518 A1 | | 2/2011 |

OTHER PUBLICATIONS

March, J., "Acids and Bases". Advanced Organic Chemistry: Reactions, Mechanisms and Structure, John Wiley & Sons, New York, 4th Edition, Chapter 8, 1992, pp. 248-272.
English language translation of Abstract of JP62000062, 2012.
J. March; Advanced Organic Chemistry Reactions, Mechanisms and Structures; 4th Edition; 1992; pp. 248-272.
J. March; Advanced Organic Chemistry Reactions, Mechanisms and Structure; 4th Edition; 1992; pp. 205, 352-357, 652-653.
The Condensed Chemical Dictionary 822 (Gessner G. Hawley Edition; 9th Edition; 1977); Concise Chemical and Technical Dictionary 1081 (H. Bennett Edition; 4th Edition; 1985); Hawley's Condensed Chemical Dictionary 1186 (Richard J. Lewis, Sr. Edition; 15th Edition; 2007.
Hawley's Condensed Chemical Dictionary; 753 (R.J. Lewis, Sr. Edition; 15th Edition; 2007).
Pearson; Hard and Soft Acids and Bases; Journal of the American Chemical Society; vol. 85; No. 22; Nov. 20, 1963; pp. 3533-3539.
Leonard et al.; Carrying Out the Reaction; Advanced Practical Organic Chemistry; 2nd Edition; 1985; pp. 129-226.
Diringer et al.; Fluorinated Pyrimidines. XXXVI. Synthesis of Some 2,4-Substituted 5-Trifluoromethylpyrimidines; Journal of Medicinal Chemistry; 13; 1970; pp. 151-152.
International Search Report, Form PCT/ISA/210, for corresponding PCT/EP2010/061840; date of mailing: Oct. 20, 2010.
Anderson, Neal G., "Assessing the Benefits of Direct Isolation Processes". Organic Process Research and Development, vol. 8, 2004, pp. 260-265.
Federsel et al., "Optimization and Scale-up of a Pd-Catalyzed Aromatic C—N Bond Formation: A Key Step in the Synthesi8s of a Novel 5-HT1B Receptor Antagonist". Organic Process Research & Development, vol. 12, 2008, pp. 512-521.
Norris et al., "Development of an Alternative Process for the Manufacture of a Key Starting Material for Cefovecin Sodium". Organic Process Research & Development, vol. 11, 2007, pp. 742-746.
Poupaert, Jacques H., "Drug Design: Basic Principles and Applications". Encyclopedia of Pharmaceutical Technology, Informa Healthcare USA, Inc., 2007, pp. 1362-1369.

* cited by examiner

*Primary Examiner* — Sun Jae Yoo
(74) *Attorney, Agent, or Firm* — Michael P. Morris; Mary-Ellen M. Devlin

(57) ABSTRACT

The present invention relates to a process for making 2,4-differentiated 5-trifluoromethyl pyrimidines and 2-amino-5-trifluoromethyl-pyrimidine derivatives, which compounds are useful in the preparation of pharmacologically active compounds.

13 Claims, No Drawings

SELECTIVE SYNTHESIS OF FUNCTIONALIZED PYRIMIDINES

FIELD OF THE INVENTION

The present invention provides new methods for the selective preparation of 2,4-differentiated 5-trifluoromethylpyrimidine building blocks as well as 2-amino-5-trifluoromethylpyrimidine derivatives which can be used as intermediates for the preparation of pharmacologically active compounds.

BACKGROUND OF THE INVENTION

In pyrimidine chemistry, for the majority of nucleophilic substitution reactions involving 2,4-functionalized pyrimidines and amines it is known that the first amine addition occurs preferentially (or exclusively) at the more reactive pyrimidine 4-position.

The reaction of pyrimidines of formula I' (particularly where X and X' are the same and are each a leaving group; most commonly a halogen, particularly chlorine) with amines of formula II usually provides mixtures of regioisomers of formulae III' (2-amino pyrimidine derivatives) and IV' (4-amino pyrimidine derivatives) (see Scheme 1 below). Examples for such unselective reactions can be found in the art, inter alia, for the electron deficient 2,4-dichloro-5-trifluoromethylpyrimidine.

Scheme 1:

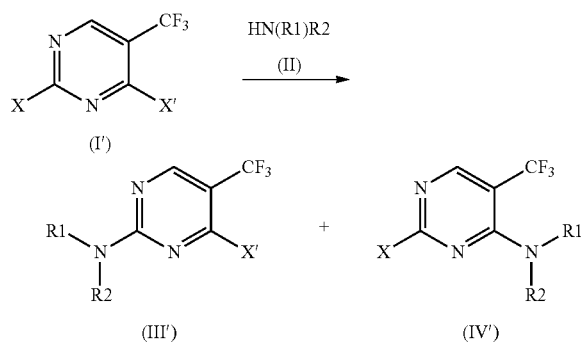

Thus, the reactions of 2,4-dichloropyrimidine derivatives with amines provide usually non-selective mixtures of 2-chloro-4-amino-pyrimidines and isomeric 2-amino-4-chloropyrimidines in such that these reactions are of limited utility not only due to their lack of selectivity (and its impact on overall yield) but also because separation of the resulting isomers is generally extremely difficult and may require preparative chromatography, which is often not desired in a process sequence.

In contrast, there are only few examples where an amine is added to a 2,4-dichloropyrimidine in a selective manner to provide preferentially the 2-amino-4-chloropyrimidine. The most notable example of this type of reaction can be found in the international application WO 2005/023780 which describes a method for selective addition of an amine functionality to the C-2 position of a $CF_3$-substituted pyrimidine ring in the presence of a Lewis Acid (namely a salt of a metal ion) and a non-nucleophilic base. However, the use of a Lewis Acid (e.g. $ZnCl_2$) is not always convenient or, in some cases, not even feasible for the desired reaction.

Thus, there remains a need in the art of methods which efficiently provide compounds of formula III'. Further, there remains a need in the art for regio-differentiation of the C-2 and C-4 position of pyrimidines which are substituted at C-5 position by $CF_3$ e.g. to obtain selective addition of amines to the usually less reactive C-2 position.

Other aims of the present invention will become apparent to the skilled man from the foregoing and following remarks.

DESCRIPTION OF THE INVENTION

It has now surprisingly been found, that by using
a phenolate leaving group (advantageously said phenolate is electron deficient phenolate, e.g. the phenolate contains one or more electron-withdrawing functional groups on the phenyl ring), such as particularly the 4-nitrophenyloxy leaving group,
as X' on the pyrimidine of formula I'; and by using
a halide leaving group (advantageously chlorine)
as X on the pyrimidine of formula I',
one can selectively replace X over X' and thus add an amine functionality to the C-2 position of the pyrimidine ring via a nucleophilic aromatic substitution reaction without needing the presence of any Lewis acidic metal ion.

Further on, by reacting pyrimidine compounds of formula I', in which X' is a leaving group selected from the group consisting of
phenyloxy optionally substituted by 1-5 suitable substituents (particularly 4-nitrophenyloxy), and X is a leaving group selected from halide (particularly chlorine), with amines of formula II (which may be employed in free form or in protonated form) in an appropriate reaction solvent (e.g. an aprotic solvent such as e.g. NMP, or a non-nucleophilic alcohol such as e.g. 2-propanol) or in a mixture of reaction solvents (such as e.g. NMP/2-propanol) and at an appropriate reaction temperature, optionally in the presence of a suitable inorganic or organic auxiliary acid or base, one can selectively obtain the corresponding compounds of formula III'.

Moreover, by reacting 2,4-dihalo-5-trifluoromethylpyrimidine (particularly 2,4-dichloro-5-trifluoromethylpyrimidine) with an appropriate hydroxy compound of formula X'—H, in which X' is a group selected from
phenyloxy optionally substituted by 1-5 suitable substituents (particularly 4-nitrophenyloxy),
in the presence of a suitable auxiliary base (which may inorganic or organic, e.g. a strong inorganic or organic base, such as e.g. diisopropylethylamine, triethylamine or potassium tert-butylate, or alkali- or earth alkali-metal hydroxide),
or, preferably, with the deprotonated (anionic) form of the hydroxy compound (e.g. the corresponding salt form of the anion, such as e.g. the metal phenolate, particularly potassium 4-nitrophenolate, which may be generated in situ),
in an appropriate reaction solvent (e.g. a lower aliphatic alcohol, such as e.g. ethanol or 2-propanol, or water) or a mixture of reaction solvents and at an appropriate reaction temperature, one can selectively introduce the hydroxyl functionality X'—H to the C-4 position of the pyrimidine ring via nucleophilic aromatic substitution reaction and thus obtain selectively corresponding compound of formula I', in which X is said halide (particularly chlorine) leaving group and X' is said phenolate leaving group as defined before.

Yet moreover, in contrast, by reacting 2,4-dihalo-5-trifluoromethylpyrimidine (particularly 2,4-dichloro-5-trifluoromethylpyrimidine) with an appropriate hydroxy compound of formula X—H, in which X is a group selected from
phenyloxy optionally substituted by 1-5 suitable substituents (particularly 4-nitrophenyloxy or 4-chlorophenyloxy),
in the presence of a suitable auxiliary base (e.g. an inorganic or, preferably, organic base, e.g. a tertiary methylamine such as e.g. N-methyl-morpholine), in an appropriate reaction solvent (e.g. a lower aliphatic alcohol, such as e.g. ethanol or 2-propanol) or mixture of reaction solvents and at an appropriate reaction temperature, one can selectively introduce the hydroxyl functionality X—H to the C-2 position of the pyrimidine ring via nucleophilic aromatic substitution reaction and thus obtain selectively corresponding compound of formula I', in which X' is said halide (particularly chlorine) leaving group and X is said phenolate leaving group as defined before.

The invention thus relates to a process comprising a method of making a compound of formula III

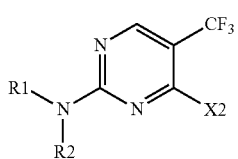
(III)

in which
X2 is a leaving group selected from the group consisting of:
phenyloxy optionally substituted by 1-5 suitable substituents,
heterocyclyl N-oxy optionally substituted by 1-5 suitable substituents, and
heteroaryl N-oxy optionally substituted by 1-5 suitable substituents; and
R1 and R2 are substituents independently selected from the group consisting of hydrogen, an aromatic group and an aliphatic group; or taken together and with inclusion of the nitrogen atom, to which they are attached, form a 4-11 membered aromatic or aliphatic ring;
said method comprising reacting a compound of formula I

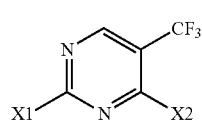
(I)

with an amine of formula II [HN(R1)R2] to form a compound of formula III,
in which
X1 is a leaving group, such as a halide (particularly chlorine).

In an embodiment of this method according to the present invention, phenyloxy optionally substituted by 1-5 suitable substituents for the use as leaving group in the meaning of the present invention may refer to phenyloxy independently substituted with 1-5 electron-withdrawing substituents on the phenyl ring, such as e.g. halo (particularly fluoro or chloro), nitro, cyano or the like.

In the context of this embodiment, illustrative examples of phenyloxy optionally substituted by 1-5 suitable substituents which may be used as leaving group in the meaning of the present invention include, without being restricted to, nitrophenyloxy like 2- or 4-nitrophenyloxy, and pentafluorophenyloxy, whereby 4-nitrophenyloxy is to be emphasized.

In another embodiment of this method according to the present invention, heterocyclyl N-oxy optionally substituted by 1-5 suitable substituents for use as leaving group in the meaning of the present invention may refer to mono- or fused bicyclic N-oxy imide derivatives.

In the context of this embodiment, illustrative examples of heterocyclyl N-oxy optionally substituted by 1-5 suitable substituents which may be used as leaving group in the meaning of the present invention include, without being restricted to, N-succinimidoxy and N-phthalimidoxy.

In another embodiment of this method according to the present invention, heteroaryl N-oxy optionally substituted by 1-5 suitable substituents for use as leaving group in the meaning of the present invention may refer to mono- or fused bicyclic N-oxy-azole derivatives or to mono- or fused bicyclic N-oxy-azinone derivatives.

In the context of this embodiment, illustrative heteroaryl N-oxy optionally substituted by 1-5 suitable substituents which may be used as leaving group in the meaning of the present invention include, without being restricted to, benzotriazol-1-oxy, 7-aza-benzotriazol-1-oxy and 1,2,3-benzotriazin-4(3H)-one-3-oxy.

An N-oxide leaving group (e.g. a heterocyclyl N-oxide or heteroaryl N-oxide leaving group) for use as X2 may be advantageously electron deficient, e.g. by substitution with one or more electron-withdrawing functional groups on the heterocyclyl or heteroaryl ring and/or by containing 1, 2, 3, 4 or more ring nitrogen atoms.

In a particular embodiment of this invention, X1 and X2 are different leaving groups. In a more particular embodiment of this invention, X1 is a halide leaving group, particularly chloride.

For example, X1 is chlorine and X2 is selected from the group consisting of:
phenyloxy optionally substituted by 1-5 suitable substituents on the phenyl ring (such as e.g. nitrophenyloxy like 2- or 4-nitrophenyloxy, pentafluorophenyloxy or 4-chlorophenyloxy),
heterocyclyl N-oxy optionally substituted by 1-5 suitable substituents on the heterocyclyl ring (such as e.g. N-succinimidoxy or N-phthalimidoxy), and
heteroaryl N-oxy optionally substituted by 1-5 suitable substituents on the heteroaryl ring (such as e.g. benzotriazol-1-oxy, 7-aza-benzotriazol-1-oxy or 1,2,3-benzotriazin-4(3H)-one-3-oxy).

In a particular preferred embodiment of this invention, X1 is chlorine and X2 is 4-nitrophenyloxy.

It is to be understood that the 4-nitrophenyloxy radical within the meaning of this invention is of the following formula:

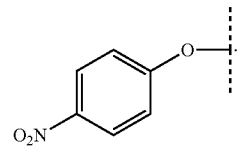

A particular aspect of the present invention is the abovementioned method characterized in that said reaction is performed as nucleophilic aromatic substitution reaction.

Another particular aspect of the present invention is the abovementioned method characterized in that said reaction is performed without the presence of a Lewis acidic metal ion.

Unless otherwise indicated, some terms used above and below to describe the compounds mentioned herein may be defined more closely as follows:

As used herein the term "aromatic", and specifically, an "aromatic group" refers to an aryl or heteroaryl radical as defined herein.

Further, an "aromatic amine" or "aromatic amine radical" refers to any amine or amine radical bound to at least one sp$^2$ carbon atom that is part of an aryl or heteroaryl group. An amine or amine radical will be referred to as an aromatic amine or radical even if the amine nitrogen is bound to a hydrogen or an $sp^a$ carbon atom, in addition to the one $sp^2$ carbon atom. Thus, for example, —HN($C_6$-$C_{10}$)aryl and —N(($C_1$-$C_6$)alkyl)(($C_6$-$C_{10}$)aryl) each refer to aromatic amine radicals as defined herein, despite the fact that each amine nitrogen is attached to non-aromatic substituents.

The term "aryl" refers to aromatic radicals such as phenyl, naphthyl, tetrahydronaphthyl, indanyl and the like. Unless otherwise mentioned, an "aryl" group may be optionally substituted with 1-3 suitable substituents, as defined herein. "Aryl" also refers to a phenyl radical fused to a non-aromatic heterocycle. Examples of such groups include but are not limited to 2-oxo-indolinyl, chromanyl, indolinyl and 2-oxo-3,4-dihydroquinolinyl optionally substituted by 1 to 3 suitable substituents.

As used herein, the term "heteroaryl" refers to an aromatic heterocyclic group usually with one heteroatom selected from O, S and N in the ring, wherein—unless otherwise mentioned—the aromatic heterocyclic group may be substituted by up to three suitable substituents as defined herein. In addition to said one heteroatom, the aromatic heterocyclic group may optionally have up to four N atoms in the ring. Examples of heteroaryl groups include but are not limited to pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents. Alternatively, any ring carbon, —CH—, of the aforementioned heteroaryl group, may be replaced by a group selected from —C=O or —$SO_2$.

"Heteroaryl" also refers to one of the aforementioned heteroaryl groups fused to a non-aromatic heterocycle. Examples of such groups include but are not limited to 1,3-dihydro-pyrrolo[2,3-b]pyridin-2-one, 3,4-dihydro-1H-[1,8]naphthyridin-2-one, 1,3-dihydro-pyrrolo[2,3-b]pyridine and 3,4-dihydro-2H-pyrano[2,3-b]pyridine.

"Aliphatic", and specifically, an "aliphatic group" refers to an alkyl, cycloalkyl, or heterocycloalkyl radical, as defined herein. Aliphatic groups may be substituted with up to three suitable substituents as defined herein.

As used herein, the term "aliphatic amine" or "aliphatic amino radical" refers to any amine or amine radical in which the amine or radical nitrogen atom is bound to an $sp^3$ carbon that is part of an alkyl, cycloalkyl, or heterocycloalkyl group. Aliphatic amine groups may be substituted with up to three suitable substituents as defined herein.

The term "alkyl" refers to $C_1$-$C_{10}$ linear or branched alkyl groups (such as methyl, ethyl, n-propyl, isopropyl, n-butyl, isobutyl, sec-butyl, tert-butyl etc.), particularly $C_1$-$C_4$ alkyl, optionally substituted by 1 to 3 suitable substituents as defined herein.

The term "cycloalkyl" or "cyclyl" refers to $C_3$-$C_{12}$ monocyclic, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonan), etc.) that is optionally substituted by 1 to 3 suitable substituents as defined herein. Bicyclic or tricyclic species may be fused, bridged or spirocyclic. Thus, examples of "cycloalkyl" or "cyclyl" groups, as defined herein, include, but are not limited to cyclopropyl, cyclobutyl, cyclopentyl, cyclohexyl, cycloheptyl, cyclohexenyl, bicyclo[2.2.1]heptanyl, bicyclo[3.2.1]octanyl, bicyclo[3.1.0]hexyl and spiro[2.4]heptyl.

The term "heterocycloalkyl" or "heterocyclyl" or "heterocycle" refers to a monocyclic, bicyclic or tricyclic group containing 3 to 9 carbon atoms and 1 to 4 heteroatoms selected from —N, —NR, —O—, —S—, —SO— and —$SO_2$—, wherein—unless otherwise mentioned—the cyclic radical is optionally substituted by 1 to 3 suitable substituents as defined herein. Bicyclic or tricyclic species may be fused, bridged or spirocyclic. Examples of such groups include but are not limited to azetidinyl, pyrrolidinyl, piperidinyl, morpholinyl, piperazinyl, tetrahydrofuranyl, oxetanyl, thiomorpholinyl, quinuclidinyl, 5-aza-spiro[2.4]heptyl and 3-aza-bicyclo[3.1.0]hexyl.

As used herein, the term "halogen" includes fluoro, chloro, bromo or iodo or fluoride, chloride, bromide or iodide.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group).

When two substituents attached to a nitrogen atom [such as in —N(R1)R2 or —N(R3)R4 or —N(R5)R6] are taken together and with inclusion of the nitrogen atom, to which they are attached, form a cyclic amine, said amine can be a monocyclic, bicyclic or tricyclic ring comprising 3 to 9 carbon atoms and 0 to 3 further heteroatoms selected from —N—, —O—, —S—, —SO— and —$SO_2$— (excluding the nitrogen atom to which the two substituents are attached).

The cyclic amine may be optionally substituted with 1 to 3 suitable substituents as defined herein. Bicyclic or tricyclic species may be fused bridged or spirocyclic. Examples of such cyclic amines include, but are not limited to, morpholine, azetidine, piperazine, piperidine, pyrrolidine, indoline, thiomorpholine.

A "suitable substituent" means a functional group which is suited for its intended function. Thus, said "suitable substituent" may be a chemically and, if desired, pharmaceutically acceptable functional group. Such suitable substituents for the aforementioned aryl, heteroaryl, alkyl, cycloalkyl, and heterocycloalkyl groups may be routinely described by those skilled in the art. Illustrative examples of said suitable substituents include, but are not limited to hydrogen, halo groups, perfluoroalkyl groups, perfluoroalkoxy groups, alkyl groups, alkenyl groups, alkynyl groups, hydroxy groups, oxo groups, alkylthio groups, arylthio groups, alkylsulfonyl groups, arylsulfonyl groups, heteroarylsulfonyl groups, alkylsulfonate groups, arylsulfonate groups, perfluoroalkylsulfonate groups, alkoxy groups, aryl or heteroaryl groups, cycloalkyl or heterocycloalkyl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups, dialkylaminocarbonyl groups, sulfonamido groups, alkylsulfonamido groups, dialkylsulfonamido groups, amido groups, N-acyl groups, arylcarbonyl groups, aryloxycarbonyl groups and the like, as well as, depending on the intended function, nitro, cyano and the like. Methylene groups may also be substituted for a carbonyl (C=O) group. Those skilled in the art will appreciate that many substituents can contain additional substituents.

In general, if residues, substituents or groups occur several times in a compound they may have the same or different meanings.

The compounds and salts prepared by the methods of the present invention may exist in several isomeric forms. All isomeric forms (e.g. all stereoisomeric forms like chiral, enantiomeric, diastereomeric or racemic forms, atropisomeric, tautomeric and all geometric isomeric forms) of the compounds and salts thereof prepared by the methods of the present invention are intended within this invention, unless the specific isomer form is specifically indicated.

Thus, e.g. the compounds and salts prepared by the methods of the present invention may exist in several tautomeric forms, including the keto and enol form, and the imine and enamine form as well as geometric isomers and mixtures thereof. The preparation of all such tautomeric forms is included within the scope of the present invention. Tautomers exist as mixtures of a tautomeric set in solution. In solid form, usually one tautomer predominates. Even though the preparation of one tautomer may be described, the present invention encompasses the preparation of all tautomers of the present compounds.

The present invention also includes the preparation of atropisomers of the compounds. Atropisomers refer to compounds that can be separated into rotationally restricted isomers.

The compounds prepared by the methods of the invention may contain olefin-like double bonds. When such bonds are present, the compounds exist as cis and trans configurations or E- and Z-isomers, and as mixtures thereof, and the present invention contemplates the preparation of all of these isomers of the described compounds.

As disclosed herein, compounds of formula III can be prepared by reaction of a pyrimidine of formula I and a primary or secondary amine nucleophile of formula II (which may be used in free or in acid addition salt form) in a suitable organic solvent or mixture of solvents. The meanings of X1 and X2 on pyrimidine of formula I include those as described above. Preferentially, X1 and X2 are different. Leaving groups X1 and X2 on pyrimidine of formula I particularly suitable for this reaction include chloride for X1 and 4-nitrophenyloxy for X2, thus preferably 2-chloro-4-(4-nitrophenyloxy)-5-trifluoromethylpyrimidine as reactant is used.

In one embodiment, this reaction of pyrimidine compounds of formula I with amines of formula II is carried out in the presence of a suitable inorganic or organic auxiliary acid, such as e.g. methanesulphonic acid or HCl (which may be generated in situ from a suitable chlorosilane in the presence of an alcohol, such as e.g. from trimethylsilylchloride/2-propanol, or, e.g., HCl in dioxane).

In another, alternative embodiment, this reaction of pyrimidine compounds of formula I with amines of formula II is carried out in the presence of a suitable inorganic or organic auxiliary base, such as e.g. alkali- or earth alkali-metal carbonate (e.g. sodium or potassium carbonate) or diisopropylethylamine.

Among these embodiments, the acid mediated variant is preferred, in particular if one or more further basic functionalities are present within the amine compound of formula II.

Primary or secondary amine nucleophiles of formula II being useful in the abovementioned reaction according to this invention include those described above. Particularly suitable amine nucleophiles of formula II for this reaction with compounds of formula I are primary aromatic amines (such as e.g. aniline derivatives) as described herein. These amine nucleophiles of formula II may be used in free form or in form of their acid addition salts (e.g. as hydrochloride, mesylate or tosylate salts), which may be either prepared in situ or applied in isolated form, in this reaction.

Appropriate organic solvents for this reaction are those solvents which are suitable for nucleophilic aromatic substitution reactions, including but not limited to non-protic solvents, such as e.g. tetrahydrofurane, 2-methyl-tetrahydrofurane or dioxane, polar solvents, such as e.g. dimethylformamide, dimethylacetamide, dimethylsulfoxide, sulfolane or N-methyl-2-pyrrolidinone (NMP) or N-ethyl-2-pyrrolidinone (NEP), and/or non-nucleophilic alcohols, such as e.g. secondary alcohols (e.g. 2-propanol, or the like) or tertiary alcohols (e.g. tert-butanol, tert-pentanol, or the like), or mixtures thereof.

The reaction temperature for this reaction may range from about room temperature to about boiling temperature of the solvent(s) used. Particularly, the reaction is run at elevated temperature. In an embodiment, NMP, 2-propanol or mixtures thereof are used as reaction solvent and the reaction temperature may range from about 30° C. to about 80° C., more preferentially from about 60° C. to about 70° C.

In the abovementioned reaction of pyrimidines of formula I with amines of formula II, by appropriate choice of the reaction solvent(s) considering their boiling temperatures the maximum achievable reaction temperature at the boiling temperature of the solvent(s) used can be adjusted as required for the reaction.

Preferably, in some embodiments, the abovementioned reaction is carried out under substantially water-free conditions (including the use of water-free reactants and solvents).

Optionally, an additional auxiliary agent, such as trimethylsilylchloride, can be used as a water scavenger in this reaction.

Preferably in this reaction of the present invention, if anilines of formula II contain one or more further basic functional groups like primary, secondary or tertiary amino groups, these further amino group(s) should be blocked e.g. via protonation, such as e.g. by using about 1 eq of a strong acid (e.g. hydrogenchloride in a water free solvent (e.g. HCl in dioxane), toluenesulfonic acid or methansulfonic acid) to give the respective acid addition salt, which are particularly suitable to be used in abovementioned reaction.

The present invention also relates to processes disclosed herein, said processes may comprise methods of making and/or reacting compounds of formulae I, III and/or III' as described herein. The present invention also relates to the intermediates (including compounds of formulae I, III or III' as disclosed herein), including their salts, isomers and salts of these isomers.

The processes described herein may be carried out in a single step or in several sequential steps. The intermediates may be isolated or synthesized in situ, with or without purification.

Isolation and purification methods are known in the art and include, for example, removing the solvent(s), precipitation (e.g. with a co-solvent), crystallization, chromatography on a suitable support material (e.g. normal or reverse phase), extraction, trituration, and the like.

Moreover, the compounds obtained may be isolated in free form or in form of their salts, or are converted thereinto. Also, the reactants used may be reacted in free form or in form of their salts (which may be prepared in situ or applied in isolated from). Corresponding processes are known for the skilled person.

When one of the (final) reaction steps or purification is carried out under the presence or formation of an inorganic or organic acid (e.g. hydrochloric acid, trifluoroacetic acid or the like), the products may be obtained—depending on their individual chemical nature and the individual nature of the acid used or formed—as free compound or containing said acid in a stoichiometric or non-stoichiometric quantity (e.g. as an acid addition salt). The acid contained can be analyzed according to art-known procedures, e.g. by titration or NMR, and, optionally, removed according to procedures familiar to the skilled person.

Optionally, free compounds of the formula III or III' as described herein may be converted into the acid addition salts thereof, e.g. for purification; corresponding processes are known to the skilled person, e.g. via acidification. Likewise, optionally, acid addition salts of the compounds of the formula III or III' may be converted into the free compounds; corresponding processes are also known to the skilled person, e.g. via neutralization.

Suitable acids for forming acid addition salts include for example, without being limited to, hydrochloric acid, methanesulphonic acid, or the like.

Salts can be obtained by reacting the free compounds with the desired acids or bases, e.g. by dissolving the free compound in a suitable solvent (e.g. a ketone, such as acetone, methyl ethyl ketone or methyl isobutyl ketone, an ether, such as diethyl ether, diisopropyl ether, tetrahydrofuran or dioxane, a chlorinated hydrocarbon, such as methylene chloride or chloroform, a low-molecular-weight aliphatic alcohol, such as methanol, ethanol or 2-propanol, or an ester, such as ethyl acetate) which contains the desired acid or base, or to which the desired acid or base is then added. The salts can be obtained by filtering, reprecipitating, precipitating with a anti-solvent for the addition salt or by evaporating the solvent. Salts obtained can be converted to other salts, e.g. by reaction with an appropriate acid or base or by means of a suitable ion exchanger. Likewise, salts obtained can be converted into the free compounds, which can in turn be converted into salts, by alkalization or by acidification. In this manner, unacceptable salts can be converted into acceptable salts.

The choice of the most appropriate procedural approach in each case may be determined by a person skilled in the art on the basis of his/her expert knowledge.

Illustrative amines of formula II [HN(R1)R2] which may be used in the reaction according to this invention may include—without being restricted to—toluidine (e.g. 2- or 4-methylaniline), 5-amino-1,3-dihydro-indol-2-one, chloroaniline (e.g. 3- or 4-chloroaniline), methoxyaniline (e.g. 4-methoxyaniline or 2-methoxyaniline), (optionally substituted amino)-aniline (e.g. N-(4-aminophenyl)-amine), (optionally substituted aminocarbonyl)-aniline or (optionally substituted aminocarbonyl)-methoxyaniline (e.g. N-{4-[R6(R5)N—C(=O)]-phenyl}-amine or N-{2-methoxy-4-[R6(R5)N—C(=O)]-phenyl}-amine or fluorine-substituted derivatives thereof (e.g. N-{2-methoxy-4-[R6(R5)N—C(=O)]-5-fluoro-phenyl}-amine), each where R5 and R6 are as defined herein), benzylamine, N-(4-methylbenzyl)-amine, N,N-dimethyl-1,4-phenylenediamine, cyclohexylamine, N-(cyclohexylmethyl)-amine, carboxyaniline (e.g. 4-carboxyaniline), carboxyanisidine (e.g. 2-methoxy-4-carboxy-aniline), carboxy(fluoro)anisidine (e.g. 2-methoxy-4-carboxy-5-fluoro-aniline), piperidine, N-methyl-toluidine (e.g. N-methyl-p-toluidine), or the like.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 2007, 4th Ed.) or in "Protecting Groups (Thieme Foundations Organic Chemistry Series N Group" by P. Kocienski (Thieme Medical Publishers, 2004).

In the reactions described herein, any reactive groups present such as carboxy-, carbonyl-, hydroxy-, amino-, alkylamino- or imino-groups may be protected during the reaction by conventional protecting groups which are cleaved again after the reaction.

For example, a protecting group for a carboxy group may be the methyl-, ethyl-, tert.-butyl- or benzyl-group, particularly the tert-butyl- or benzyl-group.

For example, a protecting group for a carbonyl group may be an acetal or ketal like the 1,3-dioxolane- or the 1,3-dioxane-group.

For example, a protecting group for a hydroxy group may be a trimethylsilyl-, tert.-butyldimethylsilyl-, acetyl-, trityl-, benzyl- or tetrahydropyranyl-group.

Protecting groups for an amino, alkylamino or imino group may be, for example, a formyl, acetyl, trifluoroacetyl, ethoxycarbonyl, tert-butoxycarbonyl, benzyloxycarbonyl, benzyl, methoxybenzyl or 2,4-dimethoxybenzyl group, and additionally, for the amino group, a phthalyl group.

Thus, e.g., a suitably protected carboxyaniline or carboxyanisidine within the meaning of this invention may be, for example, 4-amino-benzoic acid tert-butyl ester or 4-amino-benzoic acid benzyl ester or, respectively, 4-amino-3-methoxy-benzoic acid benzyl.

Thus, e.g., a suitably protected aminoaniline within the meaning of this invention may be, for example, (4-N-Boc-aminophenyl)-amine.

For reactions run under acidic or basic conditions the use of such protecting groups which are substantially stable under the chosen conditions is normally preferred.

The cleavage of a carboxymethyl- or a carboxyethyl-group can for example be carried out hydrolytically in an aqueous solvent, e.g. in water, methanol/water, 2-propanol/water, acetic acid/water, tetrahydrofuran/water or dioxane/water, in the presence of an acid such as trifluoroacetic acid, hydrochloric acid or sulphuric acid or in the presence of an alkali base as for example lithium hydroxide, sodium hydroxide or potassium hydroxide, but preferably sodium hydroxide, or aprotically in the presence of e.g. iodotrimethylsilane, at temperatures between 0° C. and 120° C., preferably at temperatures between 10° C. and 100° C.

An acetal or ketal can be cleaved with acetic acid, trifluoroacetic acid, hydrochloric acid, sulphuric acid or pyridium-p-toluene sulfonate in mixtures with water or in organic solvents like for example dichloromethane, 1,2-dichloroethane, tetrahydrofurane, dioxane, toluene or acetone at temperatures between −20° C. and 150° C., but preferably between 0° C. and 120° C.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetate, tetrahydrofurane, dioxane or glacial acetic acid, optionally with the addition of an acid such as hydrochloric acid at temperatures between 0° C. and 100° C., but preferably at ambient temperatures between 20° C. and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert-butyl or tert-butyloxycarbonyl group is preferably cleaved by treating with an acid such as trifluoroacetic acid or hydrochloric acid or by treating with iodotrimethylsilane optionally using a solvent such as dichloromethane, dioxane, methanol or diethylether.

A trimethylsilyl- or tert.-butyldimethylsilyl-group is cleaved with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, dioxane, acetonitrile or toluene at temperatures between −50° C. and 120° C., but preferably between −20° C. and 80° C.

A phthalyl group is preferably cleaved in the presence of hydrazine or a primary amine such as methylamine, ethylamine, ethanolamine or n-butylamine in a solvent such as methanol, ethanol, 2-propanol, toluene/water or dioxane at temperatures between 20 and 50° C.

Amines of formula II or V can be provided as disclosed herein or they are known or can be obtained analogously or similarly to known procedures. Such as e.g. amines of formula V, e.g. cispentacin-isopropylamide, can be obtained as described in WO 2007/135036. In a particular embodiment the amines of formula II and V are both primary amines.

The invention further relates to a process comprising a method of making a compound of formula I

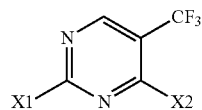
(I)

in which
X2 is a leaving group selected from the group consisting of: phenyloxy optionally substituted by 1-5 suitable substituents, heterocyclyl N-oxy optionally substituted by 1-5 suitable substituents, and
heteroaryl N-oxy optionally substituted by 1-5 suitable substituents,
particularly 4-nitro-phenyloxy; and
X1 is a leaving group, such as a halide (particularly chlorine); said method comprising reacting a compound of formula I'

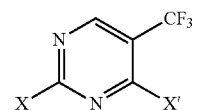
(I')

in which
X and X' are the same or different (preferentially the same), and
X is X1, and
X' is a leaving group, such as a halide (particularly chlorine), particularly 2,4-dichloro-5-trifluoromethylpyrimidine;
with a hydroxy compound of formula X2-H (particularly 4-nitrophenol),
in the presence of a suitable auxiliary base (e.g. a strong inorganic or organic base, such as e.g. diisopropylethylamine, triethylamine or potassium tert-butylate, or alkali- or earth alkali-metal hydroxide),
or, preferably,
with a deprotonated compound of formula X2-M, in which M is a metal,
in an appropriate reaction solvent (e.g. a lower aliphatic alcohol, such as e.g. ethanol or 2-propanol, or water) or a mixture of reaction solvents and at an appropriate reaction temperature.

The invention also further relates to a process comprising a method of making a compound of formula Ia

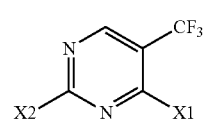
(Ia)

in which
X2 is a leaving group selected from the group consisting of: phenyloxy optionally substituted by 1-5 suitable substituents (particularly 4-nitrophenyloxy or 4-chlorophenyloxy), heterocyclyl N-oxy optionally substituted by 1-5 suitable substituents, and
heteroaryl N-oxy optionally substituted by 1-5 suitable substituents; and
X1 is a leaving group, such as a halide (particularly chlorine); said method comprising reacting a compound of formula I'

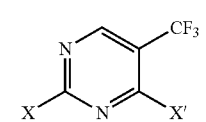
(I')

in which
X and X' are the same or different (preferentially the same), and
X' is X1, and
X is a leaving group, such as a halide (particularly chlorine), particularly 2,4-dichloro-5-trifluoromethylpyrimidine;
with a hydroxy compound of formula X2-H (particularly 4-nitrophenol or 4-chlorophenol), in the presence of a suitable auxiliary base (e.g. an inorganic or, preferably, organic base, e.g. a tertiary methylamine such as e.g. N-methyl-morpholine), in an appropriate reaction solvent (e.g. a lower aliphatic alcohol, such as e.g. ethanol or 2-propanol) or a mixture of reaction solvents and at an appropriate reaction temperature.

Preferably within the present invention, acidic hydroxy compounds which are known to the skilled person are used for the preparation of these compounds of formula I, in which X1 and X2 are the same or different (preferentially different) leaving groups according to the present invention. The hydroxyl group of these hydroxy compounds can be bonded, inter alia, to a nitrogen atom or to a phenyl ring. Known acidic hydroxy compounds may include, without being restricted to, phenols (e.g. 4-nitrophenol (HOPnp) or pentafluorophenol (HOPfp) or 4-chlorophenol), N-hydroxy-imides (e.g. N-hydroxysuccinimide (HOSu) or N-hydroxyphthalimide (HOPh)), N-hydroxy-azoles (e.g. 1-hydroxybenzotriazole (HOBt) or 1-hydroxy-7-azabenzotriazole (HOAt)), N-hydroxy-azinones (cyclic N-hydroxy-amides) (e.g. 3-hydroxy-1,2,3-benzotriazin-4(3H)-one (HOOBt, HODhbt)) and the like, as well as 2-cyano-2-(hydroxyimino)acetic acid ethyl ester.

A particular appropriate hydroxy compound of formula X2-H within the meaning of this invention is 4-nitrophenol (HOPnp).

Another appropriate hydroxy compound of formula X2-H within the meaning of this invention is 4-chlorophenol (HOPcp).

Pyrimidine compounds which can be used for the preparation of these compounds of formula I, in which X1 and X2 are the same or different (preferentially different) leaving groups according to the present invention, are those compounds of formula I' wherein X and X' are the same or different (preferentially the same) leaving groups, which may be selected from the group consisting of halide, arylsulfonate, alkylsulfonate, perfluoroalkylsulfonate, arylsulfinate and alkylsulfinate, such as 2,4-dihalo-5-trifluoromethylpyrimidine, particularly 2,4-dichloro-5-trifluoromethylpyrimidine.

In more detailed example, the compound of formula I, in which X1 is chlorine and X2 is 4-nitrophenyloxy, can be obtained from 2,4-dichloro-5-trifluoromethylpyrimidine (typically in an amount of about 1.0 equivalents) and HOPnp (e.g. in an amount of about 1.0 equivalents), preferably the deprotonated form thereof, analogously or similarly as described in the following examples, such as by deprotonating HOPnp in the presence of a suitable strong inorganic auxiliary base (such as e.g. alkali- or earth alkali-metal hydroxide like sodium hydroxide) or, especially, of a suitable strong organic non-nucleophilic auxiliary base (such as e.g. potassium tert.-butylate, N,N-diisopropylethylamine, or the like; typically in an amount of about 1.0 equivalents) in a suitable polar reaction solvent or mixture thereof, such as e.g. lower aliphatic alcohol, particularly ethanol or 2-propanol, or water, and then reacting the in situ formed 4-nitrophenolate (particularly as a solution/suspension of potassium 4-nitrophenolate in the reaction solvent) with 2,4-dichloro-5-trifluoromethylpyrimidine at a suitable reaction temperature which preferably ranges from about −20° C. to reflux temperature of the reaction solvent(s) used, e.g. about 70° C. If beneficial, the reaction is run starting at lower temperature and rising the temperature to the desired higher one.

Compounds of formula I' wherein X and X' are the same or different leaving groups independently selected from the group consisting of halide, arylsulfonate, alkylsulfonate, perfluoroalkylsulfonate, arylsulfinate and alkylsulfinate are known or can be obtained analogously or similarly to known procedures (e.g., a preparation of 2,4-dichloro-5-trifluoromethylpyrimidine is described in WO 2005/0123780).

Optionally, prior to further reaction, if the compounds of formula III obtainable via above reaction contain a functional group (e.g. —COOH), which may be temporarily protected by a suitable protecting group (e.g. by the benzyl protecting group as benzyloxycarbonyl or by the tert-butyl protecting group as tert-butyloxycarbonyl), the protecting group, if present, may subsequently be removed and the free functional group may be transformed to another functional group, such as e.g. the carboxyl group may be reacted with an primary or secondary amine of formula VI [HN(R5)R6] to give the amide group —CON(R5)R6, e.g. with the aid of a suitable coupling reagent for amide bond formation or via the respective carboxylic acid chloride, with or without isolation. In another embodiment, such conversion of a functional group may be performed later, e.g. on below-mentioned compounds of formula III' in which X' is —N(R3)R4 or —O—R7, e.g. after the reaction described herein below.

Compounds of formula III, when reacted with an oxygen, sulfur or nitrogen nucleophile (such as e.g. primary or secondary amines of formula V [HN(R3)R4] to provide 2,4-diamino products of formula III' in which X' is —N(R3)R4, or alcohols of formula VII [HO—R7] to provide 2-amino-4-oxo products of formula III' in which X' is —OR7), are useful intermediates in the preparation of pharmacological active compounds, such as e.g. protein kinase inhibitors which may be useful in the treatment of abnormal cell growth, such as cancer, in mammals. Compounds such as these are described, for example, in WO 03/030909, WO 03/032997, WO 03/078404, WO 2004/046118, WO 2004/048343, WO 2004/056807, WO 2004/056786, WO 2005/026130, WO 2005/049033, WO 2005/111023, WO 2005/113515, WO2006/021544, US 2006/025433, WO 2006/074057, WO 2006/091737, WO 2006/099974, WO 2006/117560, WO 2007/003596, WO 2007/049041, WO 2007/063384, WO 2007/072158, WO 2007/096351, WO 2007/115999, US 2007/203161, WO 2007/132010, WO 2007/140957, WO 2008/003766, WO 2008/129380, WO 2008/025556, WO 2008/045978, WO 2008/051547, WO 2008/074515, WO 2008/079907, WO 2008/077885, WO 2008/092049, WO 2008/118822, WO 2008/129380, WO 2009/012421, WO 2009/017838, WO 2009/032668, WO 2009/063240, WO 2009/071535, WO 2009/158431, WO 2009/158571, WO 2010/002655, WO 2010/046034, WO 2010/046035, WO 2010/058030, WO 2010/058032, and WO 2010/055117.

Amines of formula V or VI are primary or secondary amines, in which R3 and R4 or, respectively, R5 and R6 are substituents independently selected from the group consisting of hydrogen, an aromatic group and an aliphatic group; or R3 and R4 or, respectively, R5 and R6 taken together and with inclusion of the nitrogen atom to which they are attached form a 4-11 membered aromatic or aliphatic ring. Amines of formula V or VI include, without being limited to, cyclic amines or primary or secondary aliphatic amines, such as e.g. those mentioned herein (e.g. those wherein one of R3 and R4 or of R5 and R6, respectively, is hydrogen or alkyl and the other is optionally substituted alkyl, cycloalkyl or heterocycloalkyl as described herein), such as e.g. N-alkyl-amines, N-cycloalkyl-amines, N-heterocycloalkyl-amines, N-benzyl-amines, N-alkyl-N-methyl-amines, N-cycloalkyl-N-methyl-amines or N-heterocycloalkyl-N-methyl-amines, each alkyl, benzyl, cycloalkyl or heterocycloalkyl optionally substituted as defined herein. Examples of amines of formula V include, without being limited, cyclopropylamine, cyclobutylamine, cyclopentylamine, cyclohexylamine, N-(2-aminomethyl-5-methyl-phenyl)-N-methyl-methanesulfonamide, (1S,2R)-2-amino-1-cyclopentane carboxylic acid or its amide or isopropylamide, (1S,2R)-2-amino-cyclohexyl-carbamic acid benzyl ester or -carbamic acid tert.butyl ester, and the like. Examples of amines of formula VI include, without being limited, (1-methyl-piperidin-4-yl)-amine, (1-Boc-piperidin-4-yl)-amine, (1-methyl-piperidin-4-yl)-methyl-amine, (1-Boc-piperidin-4-yl)-methyl-amine, piperidine, morpholine, N-Boc-piperazine, N-methyl-piperazine, homopiperidine, N-methyl-homopiperazine, N-Boc-homopiperazine, and the like. The Boc or Cbz protecting group may be removed after the reaction to yield the free amine.

Alcohols of formula VII are primary, secondary or tertiary alcohols, in which R7 is an aliphatic group or an aromatic group, such as e.g. primary or secondary aliphatic alcohols or aromatic alcohols (e.g. HO-aryl, such as e.g. phenols).

It is to be understood, that certain compounds of formula III or III' as defined herein can be converted into other compounds of formula III or III', respectively, via synthetic strategies and reactions customary to the skilled person, such as e.g. comprising one or more of the methods a) to h) mentioned below.

Therefore, optionally, for example, from compounds of formula III or III' as defined herein
a) which contain a carboxyl group, the corresponding ester compounds can be obtained via esterification reaction, and/or the corresponding amide compounds can be obtained by amidification reaction;

b) which contain an ester group, the corresponding free acid compounds can be obtained via de-esterification reaction (e.g. saponification);
c) which contain a primary or secondary amino group, the corresponding amides can be obtained via acylation reaction, and/or the corresponding sulfonamides can be obtained via sulfonylation reaction;
d) which contain a hydroxyl group, the corresponding esters can be obtained via acylation reaction;
e) which contain an acylated hydroxyl group and/or an acylated amino group, the corresponding free alcohols and/or free amines can be obtained via de-acylation reaction;
f) which contain a primary or secondary amino group and/or a hydroxyl group the corresponding N-alkylated and/or O-alkylated compounds, respectively, can be obtained via N-alkylation and/or O-alkylation reaction, respectively;
g) which contain a replaceable leaving group, its replacement yielding the corresponding substituted compounds can be obtained via nucleophilic substitution reaction with N, O or S nucleophiles; and/or
h) which contain an oxidizable nitrogen or sulphur atom (e.g. aromatic or aliphatic heterocycles containing an amino- or imino-type ring nitrogen or sulphur atom), the corresponding N-oxides and/or S-oxides (including mono- and di-oxides), respectively, can via obtained by N- and/or S-oxidation reaction, respectively.

The methods mentioned under a) to h) can be expediently carried out analogously to the methods known to the person skilled in the art or as described by way of example herein.

Finally, optionally, the trifluoromethyl group of 2,4-diamino pyrimidine derivatives of formula III' in which X' is —N(R3)R4 as defined herein or of 2-amino-4-oxo pyrimidine derivatives of formula III' in which X' is —OR7 as defined herein may be hydrolyzed to form the corresponding acids, and, optionally, the thus obtained acids may be subsequently decarboxylated to form the corresponding des-trifluoromethyl derivatives. Corresponding methods are known to the skilled person.

The compounds or intermediates obtained can be further reacted without isolation or in situ, or they can be isolated and purified in a manner known per se, e.g. as described herein, for example by removing or distilling off the solvent under reduced pressure or by precipitating (e.g. by concentrating the solution, cooling and/or adding an anti-solvent), collecting, and, optionally, recrystallizing the residue obtained from one, two or more suitable organic or aqueous solvents (such as e.g. selected from the solvents mentioned herein), or subjecting it to one of the customary purification methods, such as, for example, column chromatography on a suitable support material.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

Preparation of 2-chloro-4-(4-nitrophenyloxy)-5-trifluoromethylpyrimidine a.) 12.9 g of potassium tert.-butylate are added to a solution of 16.8 g of 4-nitrophenol in 200 mL 2-propanol (exothermic reaction). The suspension is stirred for 40 minutes at ambient temperature and subsequently cooled to −15° C. to −10° C. 25.0 g of 2,4-dichloro-5-trifluoromethylpyrimidine are added slowly at −15° to −10° C. The reaction mixture is stirred 30 minutes at −15° C. to −10° C. The cooling bath is removed and the reaction mixture is stirred for 16 hours at ambient temperature (regioselectivity [HPLC] 1:2~87:13). The reaction mixture is heated to reflux and 50 mL of purified water are added. The resulting solution is slowly cooled to ambient temperature and stirred for 2 days. The precipitate is filtered and washed with purified water/2-propanol (1:1). After drying in a vacuum drying oven 27.7 g (75% of theory) regioisomerically pure colorless title product are obtained (which can be optionally re-crystallized from ethanol/water).

HPLC: $R_t$=6.4 min

[Column: Inertsil ODS-3, 5 µm; dimension: 4.0×150 mm; temperature: 20° C.; mobile phase: A: water/0.2% $KH_2PO_4$ pH 3.0, B: acetonitrile; isocratic NB (45:55); stop after 10 min; flow rate: 1.5 mL/min; detection UV 205 nm]

Alternatively, 33.7 g 4-nitrophenol are dissolved in 250 mL 2-propanol. 18.3 g aqueous sodium hydroxide solution (50%) diluted with 42 mL of purified water are added. Additionally 50 mL of purified water are added. The reaction mixture is stirred for 30 minutes at 50° C. and then cooled to −15° C. 50 g 2,4-Dichloro-5-trifluoromethylpyrimidine are added at −15° C. under vigorous stirring. An additional amount of 50 mL of cooled (−15° C.). 2-propanol is added. The suspension is stirred for 2 hours at −15° C. and then warmed up to 20° C. during 2 hours. 100 mL ethanol are added. The mixture is heated to reflux. The solution is cooled to 20° C. while seeding with the title product at about 60° C. After stirring the suspension for 30 minutes at 20° C. the precipitate is filtered and washed with a mixture of 150 mL 2-propanol and 75 mL purified water and then with 150 mL purified water. The product is dried at 50° C. in a vacuum drying oven. 54.3 g (74% of theory) regioisomeric pure colorless title product is obtained.

Yet alternatively, 0.67 g 4-nitrophenol are dissolved in 5 mL ethanol. 4.6 mL of 1 M aqueous sodium hydroxide solution are added. The mixture is cooled to −15° C. A solution of 1.0 g 2,4-dichloro-5-trifluoromethylpyrimidine in 2 mL ethanol is added at −15° C. in portions. The suspension is stirred for 1.5 hours at −15° C. to −10° C. and then warmed up to 20° C. during 3 hours. The suspension is stirred 16 hours at 20° C. The precipitate is filtered and washed with a 1:1-mixture of methanol and purified water. The product is dried in a vacuum drying oven. 1.3 g (88% of theory) of title product is obtained with a regioisomeric purity of 88:12 (2-chloro-4-(4-nitrophenyloxy)-5-trifluoromethylpyrimidine:2-(4-nitrophenyloxy)-4-chloro-5-trifluoromethylpyrimidine).

2.0 g of crude title product with regioisomeric purity of 94:6 ((2-chloro-4-(4-nitrophenyloxy)-5-trifluoromethylpyrimidine:2-(4-nitrophenyloxy)-4-chloro-5-trifluoromethylpyrimidine) are dissolved in 4 mL acetone. 10 mL of ethanol are added. 2 mL of purified water are added slowly to the solution. Precipitation starts. After 30 min additional 8 mL of purified water are added. The suspension is stirred for 5 hours at 20° C. The precipitate is filtered and washed with a mixture of ethanol/purified water and then with purified water. After drying at 40° C. in a vacuum drying oven 1.7 g regioisomeric pure title product is obtained.

Substitution of the Chlorine Atom in 2-chloro-4-(4-nitrophenyloxy)-5-trifluoromethylpyrimidine by Nucleophiles b-1.) 50.0 g of 2-chloro-4-(4-nitrophenyloxy)-5-trifluoromethylpyrimidine are dissolved in 200 mL of 1-methyl-2- pyrrolidinone (NMP). 65.6 g of the mono-4-toluenesulfonic acid salt of 4-amino-N-methyl-N-(1-methyl-piperidin-4-yl)-benzamide, 9.44 mL of trimethylsilylchloride (as a water scavenger) and 1.50 g methansulfonic acid are added. The suspension is stirred for 39 hours at 60° C. 500 mL of methylenechloride and 100 mL purified water are added. The organic phase is separated and washed subsequently with purified water, 1N aqueous sodium hydroxide solution and saturated brine. The organic phase is dried over sodium sulphate and filtered. The filtrate is evaporated under reduced pressure to obtain 84 g of crude corresponding 2-amino pyrimidine derivative product, i.e. N-methyl-N-(1-methyl-piperidin-4-yl)-4-[4-(4-nitro-phenoxy)-5-trifluoromethyl-pyrimidin-2-ylamino]-benzamide, as an oil. The oil is dissolved in 500 mL of ethanol. 500 mL tert.-butylmethylether (TBME) and 15 g of methanesulfonic acid are added. Crystallization starts and the suspension is stirred for 5 hours at ambient temperature. The precipitate is filtered, washed with ethanol/tert-butylmethyl ether (1:1) and tert.-butylmethyl ether and is dried at 40° C. in a vacuum drying oven. 61 g (62% of theory) of product N-methyl-N-(1-methyl-piperidin-4-yl)-4-[4-(4-nitro-phenoxy)-5-trifluoromethyl-pyrimidin-2-ylamino]-benzamide are obtained as mono methanesulfonic acid salt.

HPLC: $R_t$=10.8 min

[Column: Cadenza CD-C18, 3 µm; dimension: 4.6×150 mm; temperature: 20° C.; mobile phase: A: water/0.1% $KH_2PO_4$ pH 1.7 (adjusted with $HClO_4$), B: acetonitrile; gradient:NB (95:5) hold for 5 min, from NB (95:5) in 10 min. to NB (20:80), stop time: 15 min; flow rate: 1 mL/min; detection UV 200 nm]

Alternatively, 1.0 g of 2-chloro-4-(4-nitrophenyloxy)-5-trifluoromethylpyrimidine is dissolved in 5 mL of 1-methyl-2-pyrrolidinone (NMP). 1.44 g of the mono-4-toluenesulfonic acid salt of 4-amino-N-methyl-N-(1-methyl-piperidin-4-yl)-benzamide, 76 µL of trimethylsilylchloride (as water scavenger) and 60 mg methanesulfonic acid are added. The suspension is stirred for 18 hours at 55° C. 15 mL methylenechloride and 10 mL 2N sodium hydroxide solution are added. The organic phase is separated and the solvent is reduced so that 5 g of a concentrated solution remain. To this solution 20 mL 2-propanol and 0.32 g methanesulfonic acid are added. Crystallization occurs. The suspension is filtered, washed and dried to obtain 1.5 g (77% of theory) of product N-methyl-N-(1-methyl-piperidin-4-yl)-4-[4-(4-nitro-phenoxy)-5-trifluoromethyl-pyrimidin-2-ylamino]-benzamide as methanesulfonic acid salt.

b-2.) 21.4 g of 4-amino-3-methoxy-N-(1-methyl-piperidin-4-yl)-benzamide are suspended in 35 mL 1-methyl-2-pyrrolidinone (NMP) at 75° C. 11.8 mL of trimethylsilylchloride (TMSCl) and 5.9 g of 2-propanol are added (exothermic reaction). The solution is stirred for 1 h at 70° C. and a suspension develops. Then 26 g of 2-chloro-4-(4-nitrophenyloxy)-5-trifluoromethylpyrimidine are added. The reaction mixture is stirred for 17 hours at 70° C. At this temperature 300 mL acetone are added. The suspension is slowly cooled to ambient temperature and stirred for 5 hours. The precipitate is filtered and washed with acetone. After drying in a vacuum drying oven 47 g (99% of theory) of the corresponding 2-amino pyrimidine derivative product, i.e. 3-methoxy-N-(1-methyl-piperidin-4-yl)-4-[4-(4-nitro-phenoxy)-5-trifluoromethyl-pyrimidin-2-ylamino]-benzamide, are obtained as monohydrochloride salt.

HPLC: $R_t$=7.5 min

[Column: Inertsil ODS-3, 5 µm; dimension: 4.0×150 mm; temperature: 30° C.; mobile phase: A: water/0.2% $KH_2PO_4$ pH 3.0, B: acetonitrile; gradient: from NB (90:10) to NB (20:80) in 12 min., hold for 3 min at NB (20:80); flow rate: 1.5 mL/min; detection UV 220 nm]

b-3.) 1.0 g of 2-chloro-4-(4-nitrophenyloxy)-5-trifluoromethylpyrimidine and 0.77 g of 4-amino-3-methoxy-benzoic acid benzyl ester are suspended in 15 mL of 2-propanol. The suspension is heated to 50° C. and 0.08 mL trimethylsilylchloride (TMSCl) are added. The suspension is stirred for 16 hours at 50° C. The suspension is cooled to ambient temperature and stirred for 3 hours. The precipitate is filtered and washed with 2-propanol. After drying in a vacuum drying oven 1.38 g (85% of theory) of the corresponding 2-amino pyrimidine derivative product, i.e. 3-methoxy-4-[4-(4-nitro-phenoxy)-5-trifluoromethyl-pyrimidin-2-ylamino]-benzoic acid benzyl ester is obtained.

HPLC: $R_t$=5.9 min

[Column: Inertsil ODS-3, 3 µm; dimension: 2.1×50 mm; temperature: 40° C.; mobile phase: A: water/0.1% acetic acid, B: acetonitrile/0.1% acetic acid; gradient: from A/B (80:20) to NB (10:90) in 6 min, hold for 1.5 min at NB (10:90); flow rate: 1.0 mL/min; detection UV 254 nm]

b-4.) 3.50 g of 2-chloro-4-(4-nitrophenyloxy)-5-trifluoromethylpyrimidine and 2.03 g of 4-amino-3-methoxy-benzoic acid are suspended in 90 mL 2-propanol. 0.18 mL of concentrated hydrochloric acid are added. The reaction mixture is heated to reflux for 3.5 hours. The suspension is cooled to 20° C. and stirred at this temperature for 30 minutes. The precipitate is filtered and washed with 18 mL 2-propanol and 10 mL methanol. After drying in a vacuum drying oven at 50° C. 4.69 g (88% of theory) of the corresponding 2-amino pyrimidine derivative product, i.e. 3-methoxy-4-[4-(4-nitro-phenoxy)-5-trifluoromethyl-pyrimidin-2-ylamino]-benzoic acid is obtained as hydrochloride salt. 3

HPLC: $R_t$=14.1 min

[Column: Inertsil ODS-3, 5 µm; dimension: 150×4.0 mm; temperature: 30° C.; mobile phase: A: water/0.3% $KH_2PO_4$ pH=3, B: acetonitrile; gradient: A/B (85:15) 1 min, from A/B (85:15) to A/B (60:40) in 5 min, from A/B (60:40) to A/B (40:60) in 5 min, from A/B (40:60) to A/B (30:70) in 3 min, hold for 3 min at A/B (30:70); flow rate: 2.0 mL/min; detection UV 210 nm]

b-5.) To a suspension of 5.0 g of 4-amino-5-methoxy-2-fluoro-N-(1-methyl-piperidin-4-yl)-benzamide (cf. e.g. WO 2008/040951) in 20 mL 1-methyl-2-pyrrolidinone (NMP) are added 5.33 mL of a 4 M solution of hydrogen chloride in dioxan. The suspension is stirred at 45° C. for 1 hour. 5.68 g of 2-chloro-4-(4-nitrophenyloxy)-5-trifluoromethylpyrimidine are added. The reaction mixture is stirred for 17 hours at 73° C. At this temperature 40 mL acetone are added and the mixture is heated to reflux. The suspension is slowly cooled to ambient temperature. The precipitate is filtered and washed with acetone. After drying in a vacuum drying oven 7.93 g (74% of theory) of the corresponding 2-amino pyrimidine derivative product, i.e. 5-methoxy-2-fluoro-N-(1-methyl-piperidin-4-yl)-4-[4-(4-nitro-phenoxy)-5-trifluoromethyl-pyrimidin-2-ylamino]-benzamide, are obtained as monohydrochloride salt. Alternatively the hydrochloride salt of 4-amino-3-methoxy-5-fluoro-N-(1-methyl-piperidin-4-yl)-benzamide can be used.

HPLC: $R_t$=9.3 min

[Column: Zorbax SB-C18; 1.8 µm; dimension: 3.0×50 mm; temperature: 10° C.; mobile phase: A: water/0.1% $KH_2PO_4$ pH 1.7 ($HClO_4$), B: acetonitrile; gradient: from NB (85:15) to NB (50:50) in 7 min, hold for 3 min at NB (50:50), from NB (50:50) to NB (30:70) in 2 min, hold for 5 min; flow rate: 0.5 mL/min; detection UV 205 nm].

Substitution of the 4-nitrophenyloxy Group in 2-amino-4-(4-nitrophenyloxy)-5-trifluoromethylpyrimidine Derivatives by Nucleophiles c-1.) The methanesulfonic acid salt of above step b-1.) (e.g. 1.0 eq), an appropriate amine of formula V or an appropriate salt thereof (e.g. 1.1 eq) and a suitable inorganic or organic auxiliary base, such as e.g. diisopropylethylamine, triethylamine or an alkali- or earth alkali-metal carbonate (e.g. sodium carbonate, e.g. 5 eq), are suspended or dissolved in a suitable solvent, such as e.g. a solvent described herein as being suitable for nucleophilic aromatic substitution reactions (e.g. 1-methyl-2-pyrrolidinone [NMP]) and stirred optionally at elevated temperature, e.g. at 70°-85° C. for 16-24 hours. The product can be isolated according to procedures familiar to the skilled person. The reaction mixture is cooled to ambient temperature. Brine or water and an organic extractant (e.g. 2-propylacetate or methyltetrahydrofuran) are added. The organic phase is washed several times with diluted brine and/or water. The organic phase is dried over magnesium sulphate and filtered. The filtrate is evaporated under reduced pressure to obtain the corresponding crude 2,4-diamino pyrimidine derivative as product.

Optionally, the crude product is purified, such as e.g. by flash chromatography on silica gel e.g. with a suitable eluent (e.g. methylenechloride/methanol/conc. ammonia).

c-2.) The 2-amino pyrimidine derivative obtained in above step b-2.) (e.g. 1.0 eq), an appropriate amine of formula V or an appropriate salt thereof (e.g. 1.1 eq.) and a suitable inorganic or organic auxiliary base, such as e.g. diisopropylethylamine, triethylamine or an alkali- or earth alkali-metal carbonate (e.g. sodium carbonate, e.g. 5 eq), are suspended or dissolved in a suitable solvent, such as e.g. a solvent described herein as being suitable for nucleophilic aromatic substitution reactions (e.g. 1-methyl-2-pyrrolidinone [NMP]), and stirred optionally at elevated temperature, e.g. at 80° C. for 21 hours. The product can be isolated according to procedures familiar to the skilled person. The reaction mixture is cooled to ambient temperature and purred into diluted brine. An appropriate organic extractant, e.g. 2-propylacetate, is added and the organic phase is separated. The organic phase is washed several times with diluted brine, dried over magnesium sulphate and filtered. The filtrate is evaporated under reduced pressure to obtain the corresponding crude 2,4-diamino pyrimidine derivative as product. Optionally, the crude product is purified, such as e.g. it is re-crystallized from a suitable solvent or mixture of solvents (e.g. ethanol/water).

c-3.) The 2-amino pyrimidine derivative obtained in above step b-2.) or b-5 (e.g. 1.0 eq), a primary or secondary alcohol or an aromatic alcohol (e.g. a phenol derivative) and a suitable inorganic or organic auxiliary base, such as e.g. 1,8-diazabicyclo[5.4.0]undec-7en (DBU) or an alkali- or earth alkali-metal carbonate (e.g. sodium or potassium carbonate, e.g. 3-5 eq), are suspended or dissolved in a suitable solvent, such as e.g. a solvent described herein as being suitable for nucleophilic aromatic substitution reactions (e.g. 1-methyl-2-pyrrolidinone [NMP] or acetonitrile), and stirred optionally at elevated temperature, e.g. at 60° C. to 80° C. for 10-30 hours. The product can be isolated according to procedures familiar to the skilled person. Water can be added to the reaction mixture under slightly elevated temperature and the product can be crystallized. Alternatively the reaction mixture is purred into diluted brine. An appropriate organic extractant, e.g. 2-propylacetate or 2-methyl-tetrahydrofuran, is added and the organic phase is separated. The organic phase is washed several times with diluted brine, dried over magnesium sulphate and filtered. The filtrate is evaporated under reduced pressure to obtain the corresponding crude 2-amino-4-oxo-pyrimidine derivative as product. Alternatively the crude product can be purified via chromatography. Optionally, the crude product is purified, such as e.g. it is crystallized from a suitable solvent or mixture of solvents (e.g. ethanol/water or aceton/water).

Preparation of 2-(4-nitrophenyloxy)-4-chloro-5-trifluoromethylpyrimidine 11.6 g of N-methylmorpholine is added to a solution of 16.3 g of 4-nitrophenol in 200 mL 2-propanol. The solution is cooled to −5° C. 25 g of 2,4-dichloro-5-trifluoromethylpyrimidine is added slowly so that the temperature is kept below 0° C. The reaction mixture is stirred under warming up to ambient temperature for 4 hours (regioselectivity [HPLC] 1:2~7:93). 400 mL of purified water is added and the suspension is stirred for 1.5 hours. The precipitate is filtered and washed with purified water/2-propanol (2:1). After drying in a vacuum drying oven 35 g (96% of theory) crude title product is obtained as colourless solid (regioisomeric purity [HPLC] 1:2~3:97).

To improve the purity 36 g of the crude product is recrystallized from 300 mL 2-propanol/200 mL purified water. 31.6 g (90% of theory) title product is obtained (regioisomeric purity [HPLC] 1:2<1:99).

HPLC: $R_t$=6.4 min

[Column: Inertsil ODS-3, 5 μm; dimension: 4.0×150 mm; temperature: 20° C.; mobile phase: A: water/0.2% $KH_2PO_4$ pH 3.0, B: acetonitrile; isocratic A/B (45:55); stop after 10 min; flow rate: 1.5 mL/min; detection UV 205 nm]

Preparation of 2-(4-chlorophenyloxy)-4-chloro-5-trifluoromethylpyrimidine 0.25 mL of N-methylmorpholine is added to a solution of 0.23 mL of 4-chlorophenol in 5 mL 2-propanol. The solution is cooled to 0° C. 0.5 g of 2,4-dichloro-5-trifluoromethylpyrimidine are added so that the temperature is kept below 0° C. The reaction mixture is stirred for 1 hour at 0° C. and an additional hour under warming up to ambient temperature. The solvent is evaporated under reduced pressure. The residue is dissolved in methylene chloride and washed with water. The organic phase is dried over sodium sulphate and filtered. The filtrate is evaporated under reduced pressure. 0.68 g of an oil are obtained which crystallizes on standing. The crude product is purified via chromatography on silica gel using cyclohexane/ethylacetate (40:1) as eluent. 0.52 g (73% of theory) of the 2-(4-chlorophenyloxy)-4-chloro-5-trifluoromethylpyrimidine are obtained as colorless solid.

HPLC: $R_t$=4.7 min

[Column: Inertsil ODS-3, 3 μm; dimension: 2.1×50 mm; temperature: 40° C.; mobile phase: A: water/0.1% acetic acid, B: acetonitrile/0.1% acetic acid; gradient: from NB (80:20) to NB (10:90) in 6 min, hold for 1.5 min at A/B (10:90); flow rate: 1.0 mL/min; detection UV 254 nm]

What is claimed is:
1. A process for making a compound of formula III

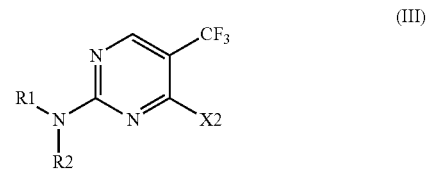

wherein

X2 is a leaving group selected from the group consisting of:
2- or 4-nitrophenyloxy, pentafluorophenyloxy, 4-chlorophenyloxy,
heterocyclyl N-oxy optionally substituted by 1-5 suitable substituents, and
heteroaryl N-oxy optionally substituted by 1-5 suitable substituents;

R1 and R2 are substituents independently selected from the group consisting of hydrogen, an aromatic group and an aliphatic group, or taken together —N(R1)R2 can form a 4-11 membered aromatic or aliphatic ring;

said process comprising reacting a compound of formula I

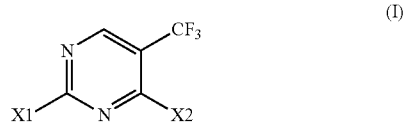

wherein
X1 is chlorine,
with an amine of formula II [HN(R1)R2] to form a compound of formula III.

2. The process of claim 1 wherein one of R1 and R2 is hydrogen and the other is an aromatic group.

3. The process of claim 1 wherein X1 is chlorine and X2 is 4-nitrophenyloxy.

4. The process of claim 1 wherein said reaction is conducted in the presence of an inorganic or organic auxiliary acid.

5. The process of claim 1 wherein said reaction is conducted in the presence of an inorganic or organic auxiliary base or diisopropylethylamine.

6. The process of claim 1 wherein said reaction is conducted in a non-protic solvent or in a non-nucleophilic alcohol or in a mixture of both.

7. The process of claim 1, wherein said reaction is conducted in a reaction solvent comprising one or more selected from N,N-dimethylformamide, N,N-dimethylacetamide, 1-methyl-2-pyrrolidinone (NMP), 1-ethyl-2-pyrrolidinone (NEP) and isopropanol.

8. The process of claim 1 wherein said reaction is conducted at a reaction temperature from about room temperature to about boiling temperature of the solvent(s) used.

9. The process of claim 1 characterized in that said reaction is conducted without any Lewis acidic metal cation.

10. The process of claim 1 further comprising the step of reacting the compound of formula III with an oxygen, sulphur or nitrogen nucleophile.

11. The process of claim 4 wherein said reaction is conducted in the presence of methanesulphonic acid or hydrogen chloride.

12. The process of claim 5 wherein said reaction is conducted in the presence of an alkali- or earth alkali-metal carbonate.

13. The process of claim 12 wherein said reaction is conducted in the presence of sodium or potassium carbonate.

* * * * *